United States Patent
Brown

(10) Patent No.: US 8,678,018 B2
(45) Date of Patent: Mar. 25, 2014

(54) METHOD OF CONDITIONING HAIR AND RECONDITIONING HAIR COLOR

(75) Inventor: Don W. Brown, Medina, MN (US)

(73) Assignee: Don W. Brown, Medina, MN (US)

(*) Notice: Subject to any disclaimer, the term of this patent is extended or adjusted under 35 U.S.C. 154(b) by 708 days.

(21) Appl. No.: 12/361,085

(22) Filed: Jan. 28, 2009

(65) Prior Publication Data

US 2009/0188515 A1 Jul. 30, 2009

Related U.S. Application Data

(60) Provisional application No. 61/024,344, filed on Jan. 29, 2008.

(51) Int. Cl.
*A61K 8/18* (2006.01)
*A61Q 5/00* (2006.01)
*A61Q 7/00* (2006.01)
*A61Q 9/00* (2006.01)

(52) U.S. Cl.
USPC .......................................... 132/202; 132/206

(58) Field of Classification Search
USPC ......... 132/202, 211, 206, 208, 209, 210, 203, 132/204, 200; 424/70.1
See application file for complete search history.

(56) References Cited

U.S. PATENT DOCUMENTS

| | | | |
|---|---|---|---|
| 3,596,806 A * | 8/1971 | Harschel | 222/190 |
| 3,839,553 A * | 10/1974 | Martinez et al. | 424/74 |
| 4,209,027 A | 6/1980 | Morganroth | |
| 4,551,330 A * | 11/1985 | Wagman et al. | 424/59 |
| 4,911,919 A * | 3/1990 | Patel et al. | 424/70.2 |
| 4,987,909 A * | 1/1991 | Snyder | 132/202 |
| 5,643,341 A | 7/1997 | Hirsch et al. | |
| 5,690,921 A | 11/1997 | Lang et al. | |
| 5,720,946 A | 2/1998 | Takeda et al. | |
| 5,843,193 A | 12/1998 | Hawkins et al. | |
| 5,960,998 A * | 10/1999 | Brown | 222/131 |
| 5,964,227 A * | 10/1999 | Collin | 132/209 |
| 5,973,000 A | 10/1999 | Magara et al. | |
| 6,056,946 A * | 5/2000 | Crudele et al. | 424/70.12 |
| 6,878,368 B2 * | 4/2005 | Ohta et al. | 424/70.19 |
| 6,908,491 B2 | 6/2005 | Fischer et al. | |
| 7,048,770 B2 | 5/2006 | Azizova et al. | |
| 2003/0074746 A1 | 4/2003 | Fischer et al. | |
| 2003/0143178 A1 * | 7/2003 | Komure et al. | 424/70.12 |
| 2004/0110650 A1 | 6/2004 | Siddiqui et al. | |
| 2005/0125913 A1 | 6/2005 | Narasimhan et al. | |

* cited by examiner

*Primary Examiner* — Robyn Doan
(74) *Attorney, Agent, or Firm* — Patterson Thuente Pedersen, PA

(57) ABSTRACT

A method of conditioning hair and reconditioning hair color comprising mixing hair conditioning solution with water to achieve a nearly full suspension of the hair conditioning solution in water, thereby producing a conditioner/water mixture. The conditioner/water mixture is heated to a temperature of at least 150° Fahrenheit. The conditioner/water mixture is applied to the hair.

20 Claims, 3 Drawing Sheets

METHOD OF CONDITIONING HAIR AND RECONDITIONING HAIR COLOR

CROSS-REFERENCE TO RELATED APPLICATIONS

This application claims priority under 35 U.S.C. §119(e)(1) to U.S. Provisional Patent Application Ser. No. 61/024,344, filed Jan. 29, 2008, entitled "Method of Conditioning Hair and Reconditioning Hair Color"; and the entire teachings of which are incorporated herein by reference.

BACKGROUND

The present disclosure relates to a method of treating hair. More specifically, the present disclosure relates to a method of conditioning hair and reconditioning hair color.

It is well known and appreciated that individuals utilize various products and treatments to achieve a particular and desired hairstyle and color. Many hair products, such as hair dyes, hair perms, hairsprays, hair gels, hair pomade, hair straighteners, flat irons, and the like can damage hair. Hair products strip away or remove needed moisture and protein from the hair leaving the hair unhealthy and discolored.

An extremely common hair treatment utilized by millions of individuals is a hair coloring treatment. There are numerous known hair coloring treatments capable of altering an individual's hair color. In particular, chemical treatments, including oxidative dye compositions, are commonly used because such treatments or compositions simultaneously de-color and dye the hair. In addition to color treatments, individuals often use various products to style their hair, such as hair perms, hairsprays, hair gels, hair pomade, hair straighteners, flat irons, and the like.

Over time, the color and/or texture of both natural and colored hair changes or "fades" as a byproduct of the unhealthiness of the hair. Color treated hair is especially susceptible to color fading, due to the harsh and severe chemicals used in the coloring process. Unhealthy hair, due to styling regimen or chemical treatment, can physically be damaged and visually appear faded.

SUMMARY

A method of conditioning hair and reconditioning hair color in accordance with the present disclosure comprising mixing hair conditioning solution with water to achieve a nearly full suspension of the hair conditioning solution in water, thereby producing a conditioner/water mixture. The conditioner/water mixture is heated to a temperature of at least 150° Fahrenheit. The conditioner/water mixture is applied to the hair.

Another method of conditioning hair and reconditioning hair color in accordance with the present disclosure comprises preparing a conditioner/water mixture having a maximum of 25% hair conditioner and having a minimum of 75% water. The conditioner/water mixture is applied to the hair. The conditioner/water mixture is heated to a temperature of at least 150° Fahrenheit.

DETAILED DESCRIPTION

A method of conditioning hair and reconditioning hair color is disclosed. By conditioning the hair, moisture, protein, and conditioning agents are added to the hair, thereby producing healthier and shiner hair. Also, improved hair color is a resulting byproduct of the conditioning/reconditioning of the hair through the disclosed method.

The following is a method for an "instant hot" method of deep conditioning hair and reconditioning hair color, whether natural or artificial. This method is derived from the need for more effective and time efficient conditioning service, whether at home or in a hair salon. Use of the disclosed method in tandem with traditional color treatments will significantly reduce time and cost to the consumer. Further, the disclosed method can serve as a hair-healthy alternative to traditional color treatments.

Artificial hair color will fade from its original tone in as little as two weeks. The disclosed method of conditioning/reconditioning hair will revive, re-establish, and extend the original artificial hair color for an additional time period, such as an additional two weeks or more, by providing moisture and protein to the chemically-treated hair. The disclosed method will also rejuvenate unprocessed and/or uncolored hair with moisture and protein, thereby greatly improving the health, texture, shine, and color of untreated hair.

The disclosed method allows the conditioning agents of a hair conditioner to penetrate the hair, colored or uncolored, through use of water and high temperatures via a conditioner/water solution or mixture at full suspension or nearly full suspension. In a full suspension solution or mixture, the conditioner/water solution or mixture cannot hold or dissolve any additional conditioner in suspension at that volume of water. In a nearly full suspension solution or mixture, only a small, additional amount of solution can be added and dissolved in the volume of water, such as less than an additional 5% of conditioner.

Figure 1:
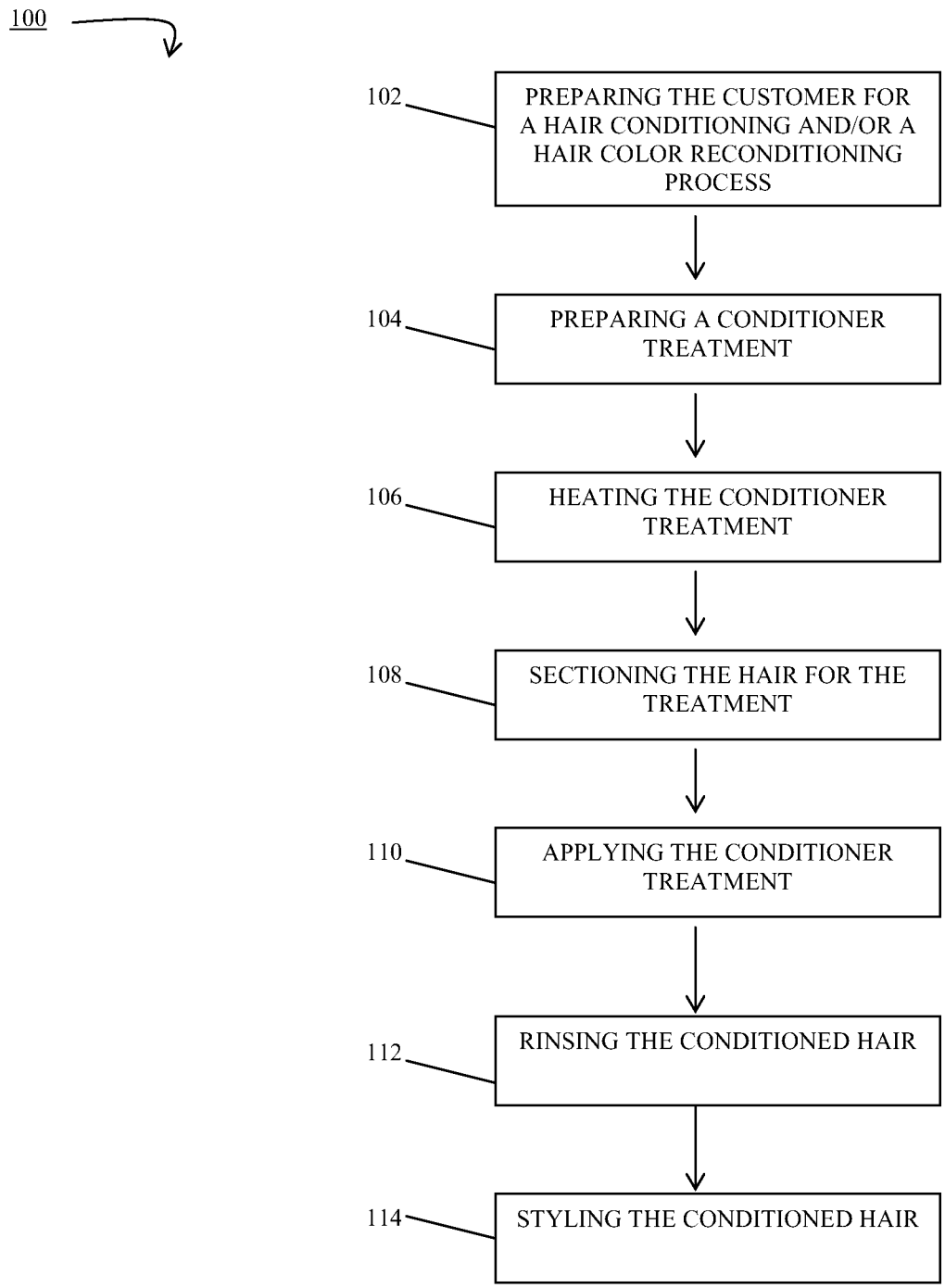
FIG. 1 is a flow chart illustrating a method of conditioning hair and reconditioning hair color in accordance with the present disclosure.

FIG. 1 is a flow chart illustrating a method of conditioning hair and reconditioning hair color in accordance with the present disclosure. At step 102, a customer is prepared for a hair conditioning and/or a hair coloring reconditioning process. It is understood that this method or process may be performed in various settings, such as in a home or at a hair salon. If at a hair salon, it is first determined that the customer wants an instant hot hair conditioning treatment. The hair conditioning treatment is then explained to the customer. Optionally, if desired or necessary, the hair may be shampooed or cleaned. The customer is then draped with a waterproof cape and neck towels are provided about the neck of the customer.

Figure 2:
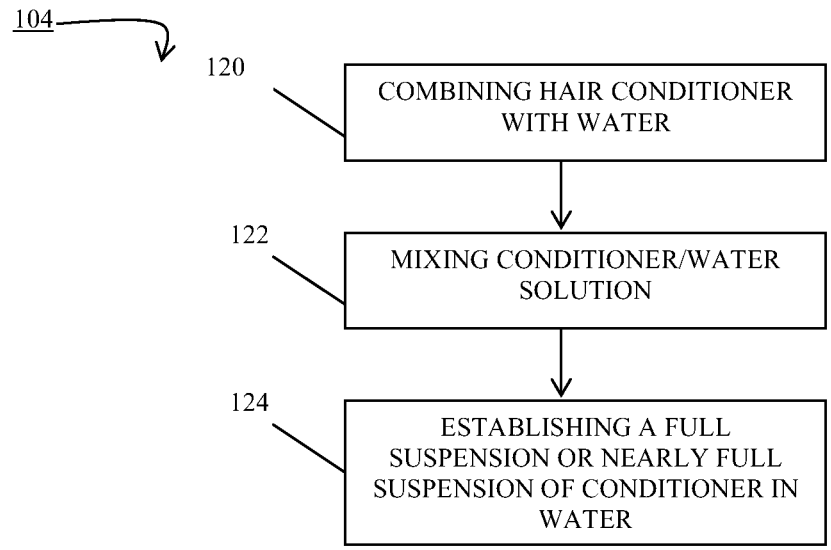
FIG. 2 is a flow chart illustrating the hair conditioner/water solution preparation in accordance with the present disclosure.

At step 104, a conditioner treatment is prepared. As shown in FIG. 2, at step 120, hair conditioner is combined with water. At step 122, the conditioner/water solution is mixed so as to dissolve the conditioner in the water. At step 124, a full or nearly full suspension of conditioner in water is established.

According to the disclosed method, hair conditioner is dissolved in water to produce a conditioner/water solution. In one embodiment in accordance with the present disclosure, one part hair conditioner is dissolved into five to ten parts water, preferably one part hair conditioner with seven parts water. In another embodiment in accordance with the present disclosure, hair conditioner is mixed with water until a full or nearly-full suspension of the hair conditioning solution in water is achieved. In yet another embodiment in accordance with the present disclosure, a conditioner/water solution includes a mixture of maximum of 25% conditioner and a minimum of 75% water. The solution can be contained and mixed in any known container, such as a bowl or a bottle, insulated or uninsulated.

Referring again to FIG. 1, at step 106, the conditioner/water solution or mixture is heated until a temperature of greater than 150° Fahrenheit is achieved. In one embodiment in accordance with the present disclosure, the conditioner/water solution or mixture is heated to 180° Fahrenheit. While heating the solution or mixture can be achieved by various means or methods, in one embodiment in accordance with the present disclosure, the solution or mixture is heated in a microwave. Due to varying microwave modules, the time necessary to achieve a conditioner/water solution temperature of 180° Fahrenheit will vary. However, a microwave timing of approximately four minutes appears to provide an approximately 180° Fahrenheit conditioner/water solution. The solution is then held in a thermal insulated bottle or bowl or similar apparatus to maintain the temperature of the solution.

At step 108, the desired hair may be sectioned in preparation for treatment.

Figure 3:
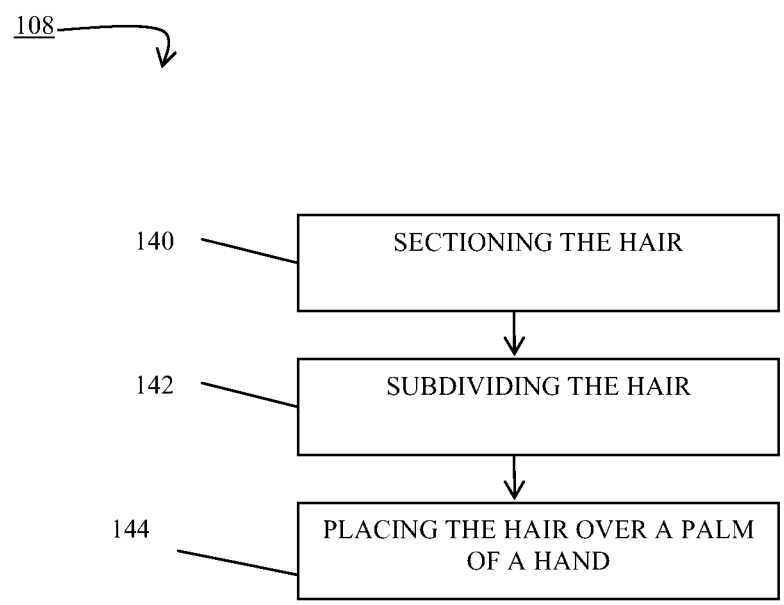
FIG. 3 is a flow chart illustrating the sectioning of hair for a conditioning treatment in accordance with the present disclosure.

FIG. 3 further shows the steps for sectioning the hair prior to treatment. At step 140, the hair is sectioned. The hair may be sectioned or partitioned into various sections, as is known in the hairdressing industry. In one embodiment in accordance with the present invention, the hair is sectioned into four parts, parting from front-to-back and from ear-to-ear. At step 142, the hair is subdivided starting with the top of one of the back sections. Horizontal partings are created in approximately ⅜ inch sections. At step 144, the approximate ⅜ inch sections are placed over a palm of a hand. In one embodiment in accordance with the present disclosure, various aides may also be used, such as foam paper, highlight sheets, or the like, rather than a palm of a hand. A color application glove may also be used to prevent heat discomfort to the hand of the applier. The scalp of the customer is avoided to prevent discomfort to the scalp.

Referring again to FIG. 1, at step 110, the conditioner treatment is applied to the desired hair. The desired hair may be wet or dry prior to treatment. The temperature of the conditioner/water solution should be maintained above 150° Fahrenheit during the entire application process, and preferably should maintain a 180° Fahrenheit temperature. In one embodiment, in accordance with the present disclosure, the conditioner/water solution can be applied to the hair via an atomizing or spraying process. In this embodiment, a spray bottle may be utilized. In another embodiment in accordance with the present disclosure, the conditioner/water solution can be applied to the hair through use of a hair brush or hair comb. In yet another embodiment in accordance with the present disclosure, the conditioner/water solution can be applied to the hair manually or by any other known means. Once the conditioner/water solution or mixture has been applied to all the desired sections and sub-sections of the hair, the hair has been conditioned and color reconditioned and rejuvenated.

At step 112, the conditioned hair can be rinsed with water to remove any excess conditioner/water solution. If preferred, at step 114, the conditioned hair can be styled.

Figure 4:
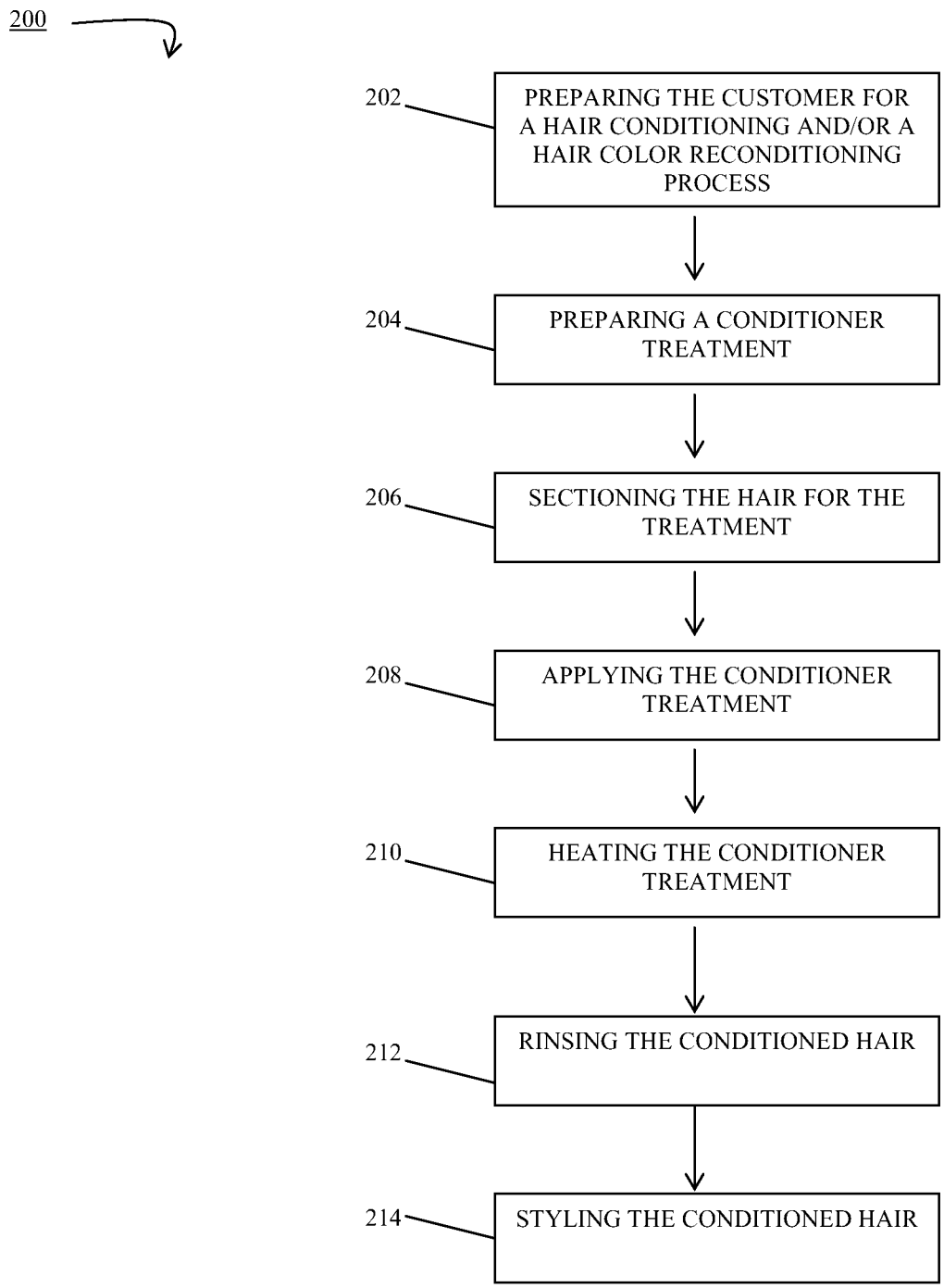
FIG. 4 is a flow chart illustrating a method of conditioning hair and reconditioning hair color in accordance with the present disclosure.

FIG. 4 illustrates flow chart 200 illustrating another method of conditioning hair and reconditioning hair color in accordance with the present disclosure. Many of the steps of flow chart 200 are similar to the steps of flow chart 100. The method of conditioning hair and reconditioning hair color shown in 200 differs from the method shown in flow chart 100 in that, at step 208, the conditioning/water solution is applied to the desired hair prior to being heated. The conditioner/water solution is applied to the hair at approximately room temperature. In one embodiment in accordance with the present disclosure, the conditioner/water solution is applied to the hair at a temperature of less than 100° Fahrenheit. At step 210, the conditioner/water solution is then heated by known means. In one embodiment in accordance with the present disclosure, the conditioner/water solution is heated through use of a flat iron, a blow dryer or any other device capable of heating the applied conditioner/water solution to a temperature above 150° Fahrenheit.

Artificially colored or damaged hair is lacking in moisture and protein. Chemical products and treatments, such as hair dyeing, hot irons, perms, straighteners, and the like, all strip both moisture and protein from hair. The disclosed method greatly revitalizes and rejuvenates damaged hair by introducing moisture, protein, and conditioning agents into the hair, thereby producing healthy, shiny hair. Healthy, shiny hair permits light to reflect off of it, thereby permitting or allowing the desired color to be seen. Therefore, conditioned, healthy, and shiny hair radiates the desired reconditioned color of the hair.

Although the present disclosure has been described with reference to preferred embodiments, workers skilled in the art will recognize that changes can be made in form and detail without departing from the spirit and scope of the present disclosure.

What is claimed is:

1. A method of conditioning hair and reconditioning hair color comprising:
    mixing hair conditioner with water to produce a solution wherein the solution is near the saturation point of the conditioner such that the solution is capable of dissolving a maximum of less than an additional 5% of conditioner;
    heating the solution to a temperature greater than 150° F.;
    maintaining the solution temperature greater than 150° F.; and
    applying the heated solution to the hair at the maintained temperature.

2. The method of claim 1, wherein the step of applying the heated conditioner/water solution of the hair further comprises:
    atomizing the heated solution proximate to the hair via a spray bottle.

3. The method of claim 1, wherein the step of applying the heated solution to the hair further comprises:
    applying the heated solution directly to the hair via a hair device of the group comprising a hair brush and hair comb.

4. The method of claim 1, wherein the step of applying the heated solution to the hair further comprises:
    manually applying the heated solution directly to the hair.

5. The method of claim 1, wherein maintaining the solution above 150° F. further comprises:
  maintaining the solution in an insulated device.

6. The method of claim 1, wherein the step of heating the solution further comprises:
  heating the solution to at least 180° F.

7. The method of claim 6, wherein the step of maintaining the solution above 150° F. further comprises maintaining the solution of at least 180° F. during the application process.

8. A method of conditioning hair and reconditioning hair color of a customer comprising:
  mixing hair conditioner with water to achieve a solution near the saturation point of the conditioner wherein the solution is capable of dissolving a maximum of less than an additional 5% of conditioner;
  heating the solution to a temperature of at least 150° F.;
  sectioning the hair into sections;
  placing the palm of a hand between the hair section and the customer;
  applying the heated solution to one of the hair sections; and,
  maintaining the solution above 150° F. during the application process such that the solution penetrates the hair while above 150° F.

9. The method of claim 8, wherein the step of applying the heated solution further comprises:
  atomizing the heated solution to the hair via a spray bottle.

10. The method of claim 8, wherein the step of applying the heated solution further comprises:
  applying the heated solution to the hair via a hair device of the group comprising of a hair brush and hair comb.

11. The method of claim 8, wherein the step of applying the heated solution to the hair further comprises:
  manually applying the heated solution to the hair.

12. The method of claim 8, wherein maintaining the solution above 150° F. further comprises:
  maintaining the solution in an insulated device.

13. The method of claim 8, wherein the step of heating the solution further comprises:
  heating the solution to at least 180° F.

14. The method of claim 13, wherein the step of maintaining the solution above 150° F. comprises:
  maintaining the solution of at least 180° F. during the application process.

15. A method of conditioning hair and reconditioned hair color comprising:
  preparing a solution, wherein;
  the solution includes a maximum of 25% hair conditioner and a minimum of 75% water;
  heating the solution to a temperature of greater than 150° F.; and
  applying the solution to the hair while the solution is at the temperature greater than 150° F., such that the solution is near the saturation point of the conditioner wherein the solution is capable of dissolving a maximum of less than an additional 5% of conditioner.

16. The method of claim 15, wherein the step of applying the solution further comprises:
  atomizing the solution proximate via a spray bottle.

17. The method of claim 15, wherein the step of applying the solution further comprises:
  applying the solution via a hair device of the group comprising of a hair brush and a hair comb.

18. The method of claim 15, wherein the step of applying the solution further comprises:
  manually applying the solution to the hair.

19. The method of claim 15, wherein the step of heating the solution comprises:
  heating the solution to a temperature of at least 180° F.

20. The method of claim 15, wherein the solution temperature is maintained above 150° F. by storing the solution in an insulated device.

* * * * *